(12) United States Patent
Lauritsch et al.

(10) Patent No.: US 7,455,453 B2
(45) Date of Patent: Nov. 25, 2008

(54) METHOD FOR RECORDING X-RAY IMAGES OF AN AREA LYING OUTSIDE A CENTER OF ROTATION OF A C-ARM SYSTEM AND THE ASSOCIATED C-ARM SYSTEM

(75) Inventors: Günter Lauritsch, Erlangen (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/890,353

(22) Filed: Aug. 6, 2007

(65) Prior Publication Data

US 2008/0089467 A1   Apr. 17, 2008

(30) Foreign Application Priority Data

Aug. 10, 2006 (DE) .................. 10 2006 037 565

(51) Int. Cl.
*H05G 1/02* (2006.01)
(52) U.S. Cl. ......................... 378/195; 378/62
(58) Field of Classification Search ............... 378/4, 378/19, 20, 62, 65, 193–197, 205, 208
See application file for complete search history.

(56) References Cited

U.S. PATENT DOCUMENTS

2006/0072699 A1* 4/2006 Mackie et al. ............. 378/4

FOREIGN PATENT DOCUMENTS

DE    10 2004 004 603 A1   8/2005

OTHER PUBLICATIONS

M. Defrise et al., Enlargement of the Region of Accurate Reconstruction in Computed Tomography from Truncated Data:P, Proceedings of the Int. Meeting on Fully Three-Dimensional Image Reconstruction in Radiology and Nuclear Medicine, Salt Lake City, UT, USA, Jul. 6-9, 2005, pp. 45-50.

I. Arai et al., "A New Class of Super-Short-Scan Algorithms for Fan Beam Reconstruction", Medical Imaging Conference, Fajardo, Puerto Rico, Oct. 23-29, 2005, IEEE Nuclear Science Symposium Conference Record, pp. 2296-2300.

L.A. Feldkamp et al., Practical Con-Beam Algorithm, J. Optical Society of America, Jun. 1984, pp. 612-619, vol. 1, No. 6.

* cited by examiner

*Primary Examiner*—Courtney Thomas

(57) ABSTRACT

The invention relates to a method for recording x-ray images with a C-arm system, which comprises an image recording system rotatable about a center of rotation in a recording plane, a number of x-ray fluoroscopic images of an area of interest of an object lying on an object supporting device are recorded at a plurality of angles of rotations by the image recording system, from which one or more cross-sectional images or a three dimensional can be reconstructed. The method is characterized in that the object supporting device is guided synchronously and in a non-colliding manner with the rotation of the image recording system, such that at every angle of rotation at which the recording of an image takes place, the area of interest of the object lies within a beam cone of the x-ray radiation beam of the image recording system.

15 Claims, 4 Drawing Sheets

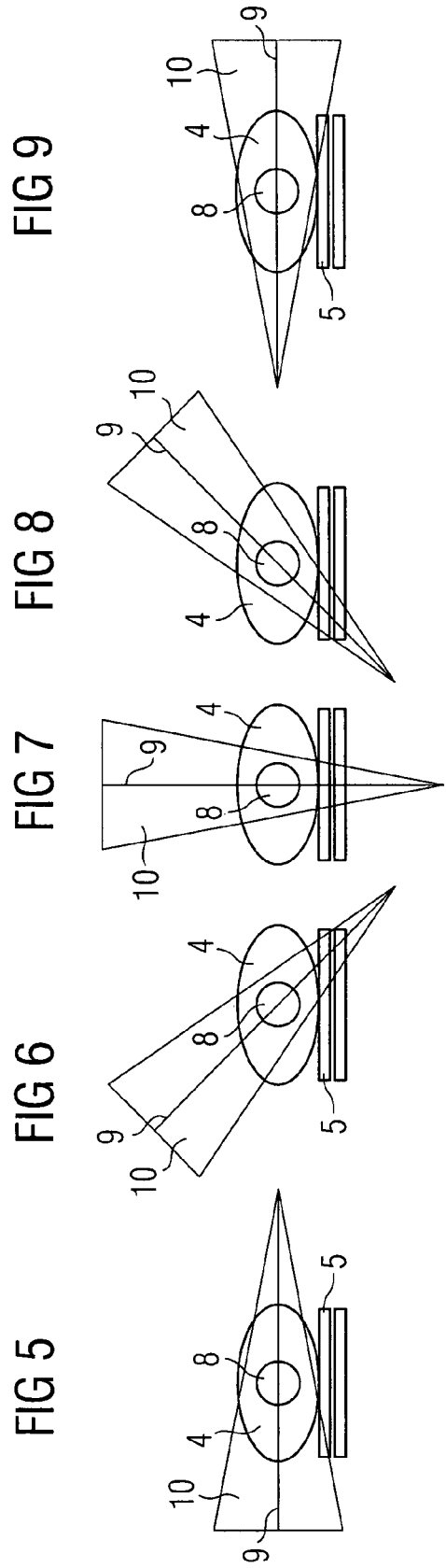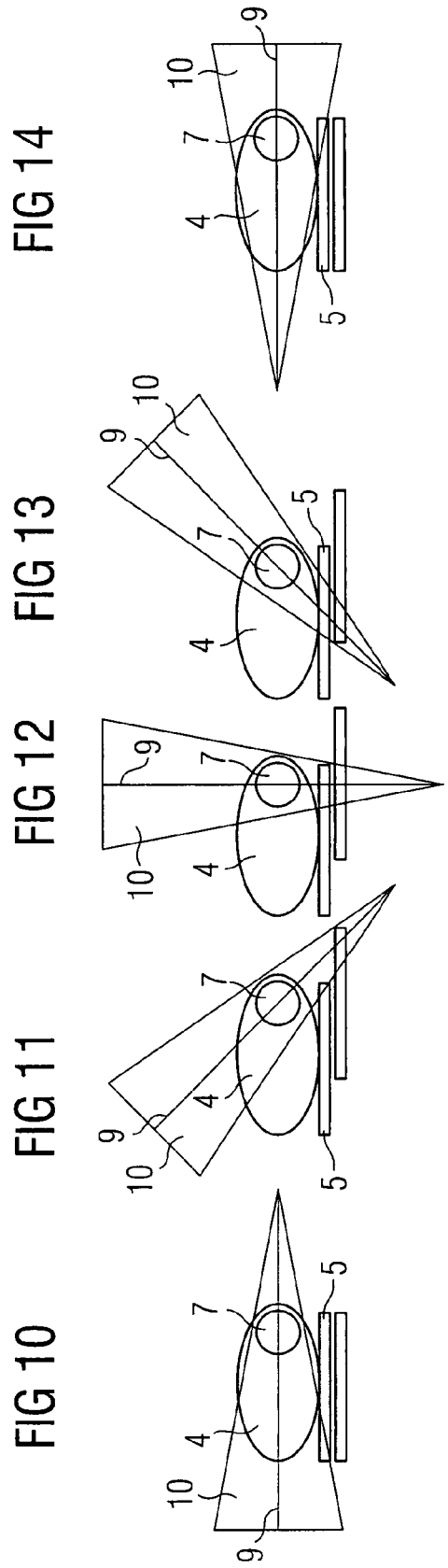

METHOD FOR RECORDING X-RAY IMAGES OF AN AREA LYING OUTSIDE A CENTER OF ROTATION OF A C-ARM SYSTEM AND THE ASSOCIATED C-ARM SYSTEM

CROSS REFERENCE TO RELATED APPLICATIONS

This application claims priority of German application No. 10 2006 037 565.3 filed Aug. 10, 2006, which is incorporated by reference herein in its entirety.

FIELD OF THE MENTION

The present invention relates to a method for the recording of x-ray images of an area of interest of an object lying outside a center of rotation of a C-arm system and a C-arm system for execution of the method.

BACKGROUND OF THE INVENTION

C-arm systems are frequently employed in medical practice. In the case of these systems, the x-ray detector and the x-ray source are affixed opposite each other on a so-called C-arm, which is embodied for the execution of a rotational movement. The image recording system can thus rotate with the x-ray source and the x-ray detector about a center of rotation, the so-called isocenter of the C-arm system. In this way, these modern C-arm systems enable the creation not just of two-dimensional fluoroscopic images, but also, through rotation of the image recording system around the patient, three-dimensional, CT-like images or cross-sectional images. The image reconstruction of the three-dimensional images or the cross-sectional images from the fluoroscopic images recorded subject to different angles of rotation takes place in a similar manner to those produced with a computer tomograph (CT). Soft tissue or, through the subtraction of contrast agent images and native images, angiographs can be represented in three-dimensional form.

The fluoroscoped object area, from which through reconstruction, a three-dimensional image can be gained, is limited by the size of the beam cone of the X-ray radiation beam. The size of the beam cone is in turn determined by the size and the distance of the x-ray detector, as a rule a flat panel detector. The area of interest of an object, known as the VOI (Volume of Interest), must lie in the isocenter of the C-arm system, so that it can be mapped by the image recording system for every angle of rotation or projection. In the case of areas of interest of objects in medical imaging which are centrally located within the cross-section of the patient, for example the head, the heart or the central abdominal area, this condition is fulfilled as a matter of course. If, however, areas at the periphery of the patient cross-section, such as the liver or the kidneys, are to be represented, problems arise on account of the above-mentioned condition. These areas can only be brought into the isocenter of the C-arm system to a limited degree, as lateral relocating of the patient or the patient support table is severely restricted by the rotating C-arm and its attached image recording system.

This is illustrated in diagrammatic form in FIG. 1, which shows a C-arm 1 with x-ray tube 2 and x-ray detector 3 in near-lateral projection during rotation around the stylized patient 4, who is positioned on the patient support table 5. A three-dimensional image of an area 6 lying within the isocenter here presents no problem. If, however, areas at the periphery of the patient cross-section are to be imaged, for example the area of interest 7 indicated in FIG. 1, the patient is currently laid on their side on the table, or the table relocated to one side (to the right in FIG. 1). The lateral relocation is, however, severely restricted because of the danger of collision with the x-ray tubes rotating about the isocenter or the rotating x-ray detector, and is thus frequently not possible to the extent necessary for the three-dimensional imaging.

SUMMARY OF THE INVENTION

The object of the present invention consists of specifying a method and an associated C-arm, with which a three-dimensional imaging of areas of interest not lying centrally within the cross-section of the object is possible.

The object is achieved with the method and the C-arm system as claimed in the claims. Advantageous embodiments of the method are the subject of the subclaims, or may be derived from the description that follows, and the exemplary embodiment.

In the suggested method for the recording of x-ray images with a C-arm system, which comprises an image recording system rotatable about a center of rotation in a recording plane, a number of x-ray fluoroscopic images of an area of interest of an object lying on the patient support table are recorded in a familiar manner by means of rotation of the image recording system, subject to various angles of rotation, from which one or more cross-sectional images or a three dimensional can be reconstructed. The method is characterized in that the object supporting device is guided synchronously and in a non-colliding manner with the rotation of the image recording system, such that at every angle of rotation at which the recording of an image takes place, the area of interest of the object lies within a beam cone of the x-ray radiation beam of the image recording system.

The present method exploits the fact that in the case of a C-arm system, although when the C-arm is in a horizontal or lateral position, only a minimal possibility of relocating the position of the object supporting device exists, at other angles of rotation, the object supporting device can advantageously be relocated horizontally or laterally by significantly greater distances without the danger of collision. By means of the suggested guidance of the object supporting device within the collision-free space synchronized with the movement of the C-arm it is ensured that the area of interest lies within the beam cone of the x-ray radiation beam upon each recording of a fluoroscopic image. The central beam of the x-ray radiation beam directed towards the x-ray detector by the x-ray tube thus always pass largely through the area of interest at this angle of rotation, so that this area is completely imaged. This is the prerequisite for the correct reconstruction of one or more cross-sectional or one three-dimensional image of this area from the recorded fluoroscopic images.

Use of the present method thus only demands that the object supporting device be capable of being relocated transversely relative to the so-called system axis or z-axis of the C-arm system with a suitable, in particular motorized drive and a control device, which actuates the drive synchronously with the movement of the C-arm and thus the rotation of the image recording system, in order to perform the tracking movement described above.

The initial position of the particular area of interest relative to the center of rotation of the C-arm device, which is as a rule in a fixed location, can here be entered into the control device, for example by the user, in the form of a lateral distance. The possibility also exists, of course, of producing one or more survey radiographs of the object without tracking movements, and displaying these on a visual display unit for the user, who can mark the area of interest on these. In this way, the original distance of the area of interest from the center of rotation can also be automatically determined by an imaging computer belonging to the C-arm system. The maximum possible collision-free lateral relocation of the object supporting device at the different angles of rotation of the C-arm must be determined in advance for the C-arm system concerned, and can, for example, be pre-stored in the control device by the manufacturer. The synchronization of the rotation of the image recording system or C-arm with the tracking of the object supporting device here presents no problems, as the angle of rotation of the C-arm at any given moment must also be recorded up to this point for the subsequent reconstruction of three-dimensional images for each image recording, and is thus known to the system.

The proposed C-arm system for implementing the method here comprises, in a known manner, a motor-driven C-arm to perform a rotational movement about a center of rotation, an X-ray image recording system attached to the C-arm, an object supporting device upon which an object can be positioned within the center of rotation of the C-arm and a control device to control the rotation of the C-arm and to control the image recording system for recording x-ray fluoroscopic images at different angles of rotation. The C-arm device of the present invention is characterized in that the object supporting device includes a drive for horizontal movement parallel to the recording plane, the control device being embodied in such a way that when required it causes this drive to perform a collision-free lateral tracking movement synchronously with the rotation of the C-arm, such that an area of interest of the object lies within a beam cone of an x-ray radiation beam of the image recording system.

As a rule, the course taken by the C-arm relative to the object during a tracking movement of this kind largely describes an ellipse. The projection matrices necessary for the three-dimensional image reconstruction can here be obtained without problem for each of the angles of rotation by means of a corresponding calibration of this trajectory with a calibration phantom, as is known from the normal circular case. By means of this calibration it is then possible to reconstruct the three-dimensional volume from the data obtained, that is the image data from the fluoroscopic images obtained subject to the different angles of rotation, for example using the approximative Feldkamp method (L. A. Feldkamp and others, "Practical Cone-Beam Algorithm", J. Opt. Soc. Am. A1 (1984), pp. 612 through 619).

An additional advantage of the present method and the associated C-arm system of device lies in the fact that the disadvantage of truncated projections can be avoided here. These truncated projections occur when the x-ray radiation beam does not completely encompass the area of interest in individual projections, that is when the area of interest protrudes beyond the beam cone of the x-ray radiation beam. In this case, precise reconstruction of the area of interest is no longer possible. If, however, as is enabled by the present method, part of the periphery of the patient is contained in the VOI, that part of the VOI can be precisely reconstructed which can be linked with the periphery by line segments, where the line segments must be wholly contained within the VOI. Details of this may be found in M. Defrise at al., "Enlargement of the Region of Accurate Reconstruction in Computed Tomography from Truncated Data", Proceedings of the Int. Meeting on Fully Three-Dimensional Image Reconstruction in Radiology and Nuclear Medicine, Salt Lake City, Utah, USA, Jul. 6 to 9, 2005, pp. 45 through 50 or from I. Arai et al., "A New Class of Super-Short-Scan Algorithms for Fan Beam Reconstruction" at the Medical Imaging Conference, Fajardo, Puerto Rico, Oct. 23-29, 2005, published in the IEEE Nuclear Science Symposium Conference Record, pp. 2296-2300.

BRIEF DESCRIPTION OF THE DRAWINGS

The present method and the associated C-arm system are described in greater detail on the basis of an exemplary embodiment in conjunction with the drawings, where:

FIGS. 5 to 9 show a stylized rotation of a C-arm around a patient without relocation of the patient support table;

FIGS. 10 to 14 show the stylized rotation of a C-arm around a patient, with simultaneous lateral relocation of the table.

DETAILED DESCRIPTION OF THE INVENTION

Figure 1:
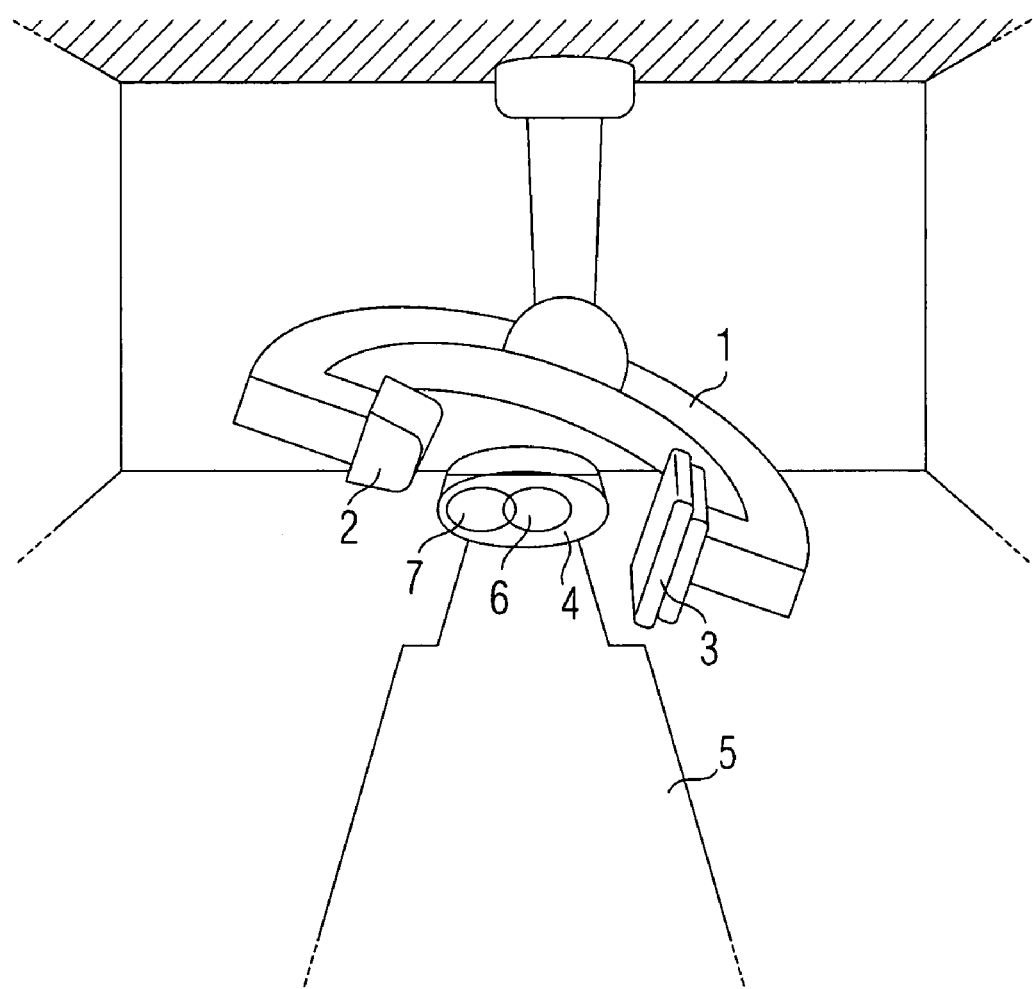
FIG. 1 shows an example of the relationships in a C-arm device, with an approximately lateral position of the C-arm.

FIG. 1 shows an example of a C-arm device, in which the C-arm 1 is located in a near-horizontal rotational position. An area 6 of the patient 4 represented in stylized form can be encompassed at all angles of rotation during the rotation of the C-arm 1 and subsequently represented according to a three-dimensional image reconstruction. If, however, an area of interest 7 at the periphery of the patient cross-section is to be imaged, the patient cross-section would have to be moved to the right. This is, however, only possible to a limited extent due to the rotation of the C-arm and the restricted space conditions in the case of lateral projection, in particular through limitations resulting from x-ray tube 2 and x-ray detector 3, and is thus insufficient for later three-dimensional reconstruction of the area of interest 7.

FIGS. 5 to 9 show the stylized rotation of the C-arm around the patient 4 in the case of a static arrangement of the patient support table 5. The volume 8 to be reconstructed here lies largely in the central beam 9 of the x-ray radiation beam or beam cone 10, so that the volume 8 of interest can be imaged without further action. If, however, the area of interest 7 lies at the left-hand periphery of the patient cross-section, then this can be completely encompassed with the lateral projections (FIG. 5/FIG. 9), but not at other angles of projection, such as, for example, in the AP projection (FIG. 7).

Figure 2:
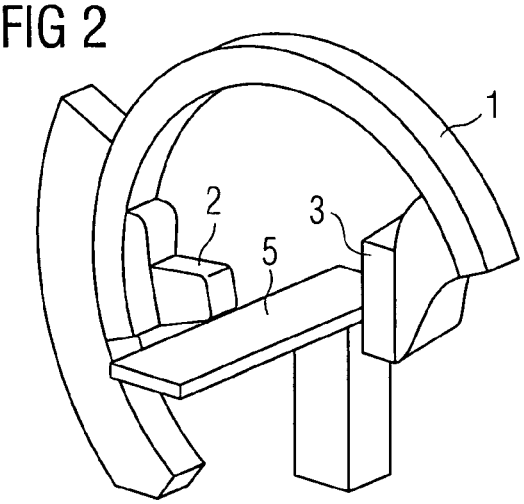
FIGS. 2 to 4 show the spatial relationships in the case of a rotation of C-arm for three different angles of rotation of the C-arm.
Figure 3:
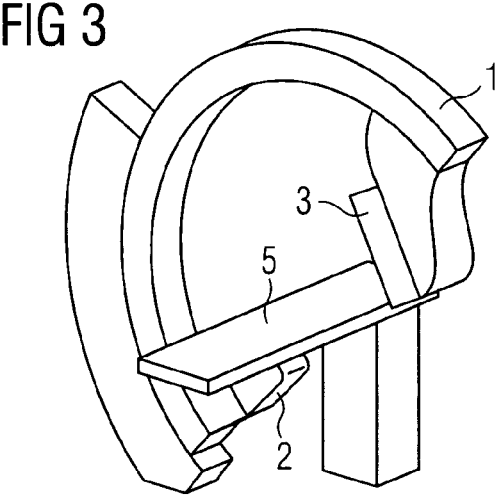
Figure 4:
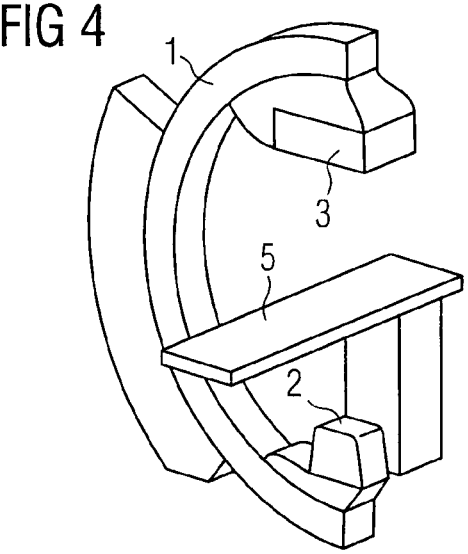

In the present method and the associated C-arm system, the different spatial relationships are now made use of, as they exist within the different rotational positions of the C-arm. These spatial relationships may be seen in the FIGS. 2 to 4. While the image recording system is in the lateral position the possibilities for moving the patient support table 5 are severely limited, in the vertical position (AP position: FIG. 4), almost any lateral relocation of the patient support table is possible without the danger of collision, In intermediate positions, for example in the rotational position shown in FIG. 3, a commensurately lesser lateral relocating of the table can still be performed without hindering the rotation, which is still greater than that possible in the lateral position.

In the present method, these different spatial relationships are exploited in order to relocate the patient support table 5 in the transverse direction relative to the patient (y-direction) using a motorized drive. Shifting the table in a longitudinal direction (Z-direction) is as a rule already possible in the case of known C-arm systems. In the present method, the patient support table 5 is relocated laterally synchronously and depending on the angle of rotation at that particular moment, in order to keep the area of interest 7 in the beam cone 10 of the X-ray radiation beam, so that if possible the central beam 9 of the X-ray radiation beam passes through the area of interest 7 each time an x-ray image is recorded. This may be seen on the basis of FIGS. 10 to 14, which show the lateral relocating of the patient support table 5 depending on the angle of rotation.

If during the rotation the C-arm is in the lateral position, then as a rule at the start and the end of the rotation, the patient support table 5 in this example remains in the center, that is to say is not relocated in the y-direction, in order not to hinder the rotation of the C-arm in this position (cf. FIG. 10/FIG. 14). If the C-arm rotates further, the table 5 is gradually relocated to the left or right, depending on the angle of rotation. The distance relocated here depends upon the position of the area of interest 7 relative to the center of rotation with the table not moved from its location. The relocation takes place in such a way that the area of interest always lies largely within the central beam 9 of the projection, as can be seen in the FIGS. 11 to 13. If the C-arm is in the AP position, the table 5 is displaced by the defined maximum distance. In this position this is possible without problems, so that here too, the rotation of the C-arm is not hindered (cf. FIG. 12). The maximum displacement for the different angles of rotation must fundamentally be limited such that the displacement does not hinder the rotation at the intermediate angles.

The proposed method guarantees that the VOI lies largely within the central beam, and can thus subsequently be reconstructed fully and with a high level of quality.

By means of a simple augmentation of known C-arm devices, the method enables the reconstruction of volumes at the periphery of the patient cross section, for example also of the liver and kidneys. The method also enables the use of precise reconstruction algorithms.

Figure 15:
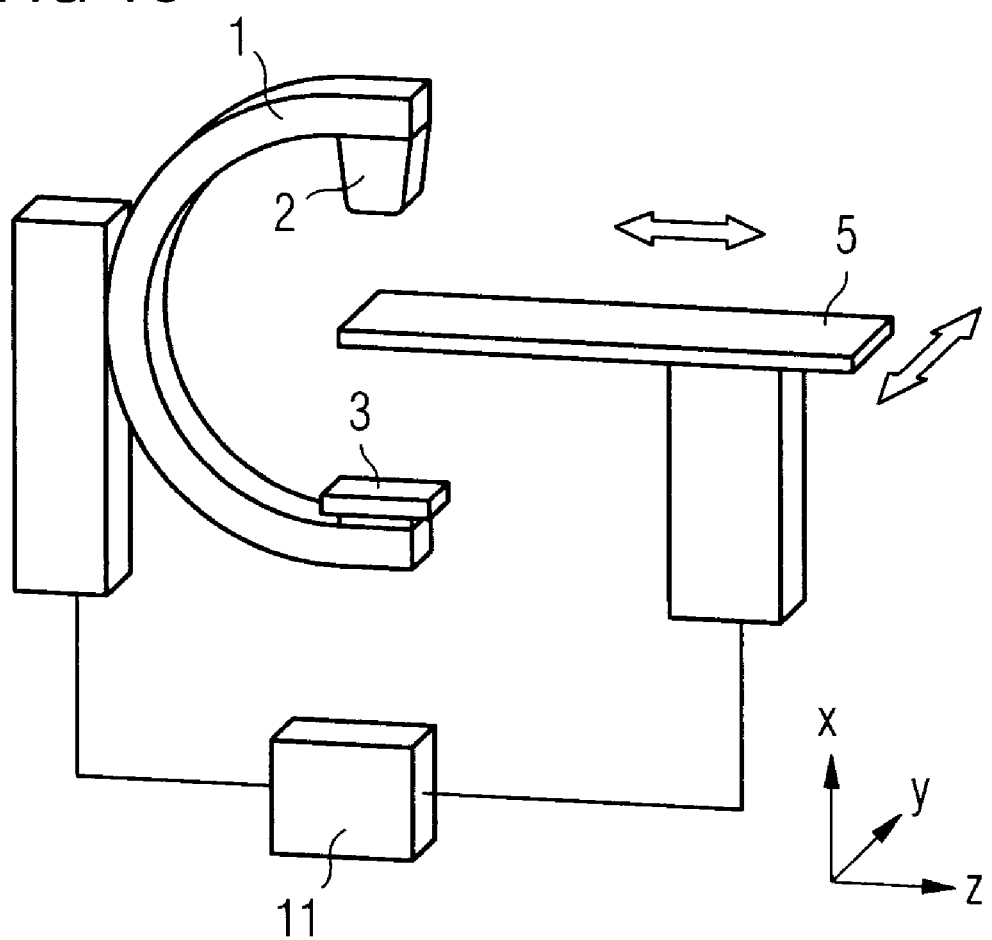
FIG. 15 shows a diagrammatic representation of a C-arm device according to the present invention.

Finally, FIG. 15 shows, still in highly diagrammatic form, the structural principles of the present C-arm device. The C-arm device has a C-arm 1 rotatable about an axis of rotation, to which are attached, opposite in each other in a known manner, an x-ray tube 2 and an x-ray detector 3. Control of the rotation of the C-arm 1 and of the image recording is performed by a control unit 1, which is also connected to the motorized drives for the patient support table 5. The patient support table 5 has a drive for relocation in the z-direction and a drive for relocation in the y-direction. The control unit 11 is here embodied such that it actuates the drive for the relocation of the patient support table synchronously with the rotation of the C-arm 1. Fundamentally, the relocation in the Z- and y-direction can take place in the known manner by means of linear axes attached to the patient support table.

The invention claimed is:

1. A method for recording x-ray images of an area of interest of an object, comprising:
    rotating an image recording system about a center of rotation;
    recording the x-ray images at a plurality of angles of rotation by the image recording system while rotating the image recording system; and
    synchronously relocating an object supporting device while rotating the image recording system so that the area of interest lies within a beam cone of x-ray radiation beams of the image recording system at the angles of rotation.

2. The method as claimed in claim 1, wherein the area of interest lies outside the center of rotation.

3. The method as claimed in claim 1, wherein the object supporting device is relocated without colliding with the image recording system.

4. The method as claimed in claim 1, wherein the object supporting device is relocated horizontally.

5. The method as claimed in claim 1, wherein the object supporting device is relocated from a zero distance when the image recording system is in a horizontal position to a maximum distance when the image recording system rotates to a vertical position.

6. The method as claimed in claim 1, wherein a cross-sectional image or a three dimensional image of the area of the interest is reconstructed from the x-ray images.

7. A C-arm system for recording x-ray images of an area of interest of an object, comprising:
    a C-arm that rotates about a center of rotation in a recording plane;
    an image recording system attached to the C-arm that is rotated by the C-arm and records the x-ray images of the area of interest at a plurality of angles of rotation; and
    an object supporting device that is synchronously relocated while rotating the image recording system so that the area of interest lies within a beam cone of x-ray radiation beams of the image recording system at the angles of rotation.

8. The C-arm system as claimed in claim 7, further comprising a control device that controls the rotation of the C-arm and the recording of the x-ray images.

9. The C-arm system as claimed in claim 8, wherein the control device actuates a drive that relocates the object supporting device.

10. The C-arm system as claimed in claim 7, wherein the object supporting device is relocated horizontally or at least approximately parallel to the recording plane.

11. The C-arm system as claimed in claim 7, wherein the object supporting device is relocated from a zero distance when the image recording system is in a horizontal position to a maximum distance when the image recording system rotates to a vertical position.

12. The C-arm system as claimed in claim 7, wherein a cross-sectional image or a three dimensional image of the area of the interest is reconstructed from the x-ray images.

13. The C-arm system as claimed in claim 7, wherein the C-arm is a motor-driven or robot-controlled C-arm.

14. The C-arm system as claimed in claim 7, wherein the area of interest lies outside the center of rotation.

15. The C-arm system as claimed in claim 7, wherein the object supporting device is relocated without colliding with the image recording system.

* * * * *